US007674233B2

(12) United States Patent
Young et al.

(10) Patent No.: US 7,674,233 B2
(45) Date of Patent: *Mar. 9, 2010

(54) METHOD AND APPARATUS FOR FOCUSSING ULTRASONIC ENERGY

(76) Inventors: Michael John Radley Young, Bremridge House, Bremridge, Ashburton, Newton Abbot, South Devon, TQ13 7JX (GB); Stephen Michael Radley Young, Bremridge House, Bremridge, Ashburton, Newton Abbot, South Devon, TQ13 7JX (GB)

( * ) Notice: Subject to any disclaimer, the term of this patent is extended or adjusted under 35 U.S.C. 154(b) by 973 days.

This patent is subject to a terminal disclaimer.

(21) Appl. No.: 10/502,919

(22) PCT Filed: Jan. 28, 2003

(86) PCT No.: PCT/GB03/00349

§ 371 (c)(1),
(2), (4) Date: Jan. 14, 2005

(87) PCT Pub. No.: WO03/065347

PCT Pub. Date: Aug. 7, 2003

(65) Prior Publication Data

US 2005/0143677 A1 Jun. 30, 2005

(30) Foreign Application Priority Data

Jan. 29, 2002 (GB) ................................ 0201978.4
May 28, 2002 (GB) ................................ 0212187.9

(51) Int. Cl.
*A61H 1/00* (2006.01)
*G10K 11/30* (2006.01)
*A61B 8/14* (2006.01)

(52) U.S. Cl. ............................ 601/2; 367/150; 600/459

(58) Field of Classification Search ................. 600/437, 600/439, 459; 601/2-4; 367/150
See application file for complete search history.

(56) References Cited

U.S. PATENT DOCUMENTS 3,903,990 A 9/1975 Yasuaki
4,044,273 A 8/1977 Kanda et al.
4,193,473 A * 3/1980 Hartemann ................. 181/176
5,365,024 A * 11/1994 Hasegawa et al. ........... 181/176
6,200,491 B1 3/2001 Zesch et al.
2001/0023326 A1 9/2001 Spector

FOREIGN PATENT DOCUMENTS

WO WO 01 02055 11/2001

* cited by examiner

*Primary Examiner*—Eric F Winakur
*Assistant Examiner*—Michael T Rozanski
(74) *Attorney, Agent, or Firm*—Carter, DeLuca, Farrell & Schmidt, LLP

(57) ABSTRACT

The apparatus comprises an ultrasonic vibration generator (1) and a lens (2) affixed thereto adapted to focus the ultrasonic vibration at a predetermined zone. It may be used to destroy certain types of cancerous cell which lie close beneath the surface, such as skin cancers and other melanomas. Other cosmetic skin treatments may also be carried out, such as restructuring collagen molecules in order to tighten and restructure skin tissue, depilation and to destroy dyed tissue and thereby aid removal of unwanted tattoos.

16 Claims, 9 Drawing Sheets

Longitudinal Response of D10R625-1 at 12500000 Hz.

Longitudinal Response of D25R15625-1 at 1400000 Hz.

METHOD AND APPARATUS FOR FOCUSSING ULTRASONIC ENERGY

The present invention relates to a method and apparatus for focussing ultrasonic energy. The apparatus and method may be used, inter alia, for treatment of tissue, especially subcutaneous tissue, utilising non-invasive focussed ultrasound.

The term focussing when applied to sound waves has subtly different meanings from the generally understood principles surrounding optical focussing. A light beam is focussed by a lens so that a planar beam of light is directed to a point of convergence (and subsequent divergence). In this case the lens is not affected by the electromagnetic beam as it travels through the device.

Ultrasound is generated by a vibrating device. If the device is a curved piezo-electric transducer crystal then the curved surface of the crystal emits a sound wave propagating normally to the surface. This wave converges over a common region. The essential difference between the optical and the ultrasonic is that the distance of the point of convergence of the sound wave from the "lens" is dependent upon the mode of resonance in the vibrating device. The case of a curved piezoelectric ceramic transducer (PZT) crystal is relatively simple, since essentially only a single mode of resonance should be possible.

However, a piezo ceramic generator and a focussing element may be deliberately close-coupled, using some form of epoxy or other cement. When this approach is taken, the simple theory is inadequate to predict focal plane position and beam intensities. Errors of up to 50% are apparent when determining the properties of small diameter acoustic lenses.

If a disc PZT is bonded to a disc of metal to produce a combination transducer, then multiple modes of resonance become possible, and the effects of changes in mode are extremely complex. In very general terms, if the free face of the metal disc is given a convex radius then most modes of resonance result in a radiating beam, i.e. divergent. Conversely, if the free face of the metal disc is given a concave radius then the transmission path of the "beam" will reduce in diameter, before subsequently increasing. This convergence will vary with the mode of resonance in degree, in the minimum diameter of the transmission path attained, and in its position from the lens.

Finite element techniques can accurately model complex physical systems which consist of two or more solid materials and an essentially fluid phase representing a target material. If it is possible to determine the transducer/lens geometry to achieve particular focussing characteristics, it will greatly simplify the task of designing and building focussed arrays of transducers with combined lens systems.

The finite element model may be used to predict the geometry of axisymmetric lens transducer combinations taking into account all factors affecting the vibrational modes generated in the solid components of the system. The analytical mesh may be extended into the fluid phase to generate beam shape and confirm the focussing characteristics of the device.

Curved PZT transmitters (operating in the MHz bands) are used in various medical applications, but they suffer from at least two inherent limitations. They are expensive to produce and they are essentially fragile.

The former problem is simply a function of the production process. The latter arises from the high output requirements for medical applications and the minimal thickness of the ceramic in order to achieve resonance at MHz frequencies.

Systems are known from our Patent Application No GB 2367500A in which a lens is disposed adjacent to a PZT. However, the focussing of such systems has been found to be difficult since the approach taken has not appreciated the complexity of the problem.

Combination transducers, i.e. transducers having a lens firmly attached to the PZT, should point towards a single solution to these problems. Firstly, flat disc PZTs are a fraction of the cost of curved ceramics, and may be produced in all possible dimensions. Secondly, bonding a flat PZT to an aluminium plate, using epoxy adhesive, results in a highly durable system.

Such combination transducers can be further improved by curving a face of the lens plate. However the focussing of such transducers is much more complex than has hitherto been thought.

It is therefore an object of the invention to provide a combination lens giving improved beam focussing.

In general, tissue which may be treated by the method and using the apparatus includes subcutaneous blood vessels, unsightly thread veins, selected cancer tissue, and the like. The apparatus may be used for haemostatic cutting and cauterising of blood vessels. It may also be used in other, non-medical, areas where it is desired to apply high intensity energy to a small target zone.

One tissue type which may benefit from such treatment comprises fine arteries and veins lying closely beneath the dermis. These may become visible in quite random areas, and where they are visible through the dermis in a localised area, these arteries or veins may constitute a serious visual skin blemish, known sometimes as "spider veins."

It is known to remove or treat such blood vessels either using laser energy or by forms of invasive surgery so that the blood supply to that particular part of the vascular system is permanently interrupted and the unsightly blemish may be removed.

However, such known methods of treatment may cause collateral damage to the tissue of the patient being treated or may require lengthy recovery periods.

Similarly, it is well known that certain types of cancerous cell may lie close beneath the surface, such as skin cancers and other melanomas. Such cancers can sometimes be treated by means of laser irradiation, but there may again be damage to surrounding tissue and to the outer layers of the dermis and this may be unacceptable.

Cosmetic skin treatments may also be carried out in similar ways.

Collagen molecules may be restructured in order to tighten and restructure skin tissue, using a focussed beam.

Depilation may presently be carried out by painful treatments such as electrolysis, or temporarily by waxing, shaving or plucking. A beam of energy focussed on each follicle would destroy the hair and prevent further growth.

A focussed beam may also be used to destroy dyed tissue and thereby aid removal of unwanted tattoos.

It is thus a further object of the present invention to provide a method and apparatus for treatment of surface or subcutaneous tissue which obviates the above disadvantages.

According to a first aspect of the present invention, there is provided an apparatus for focussing a beam of ultrasonic vibration comprising means to generate ultrasonic vibrations and lens means affixed to said generating means and adapted to focus said ultrasonic vibration at a predetermined zone.

The lens means may be piano-concave.

The lens means may comprise titanium, titanium alloy, aluminium, aluminium alloy, or a mixture containing such materials.

The lens means may comprise a plurality of individual lens facets.

In this case, the plurality of individual lens facets may be affixed to a single generating means.

At least some of said facets may have a substantially coincident centre of their radius of curvature.

At least some of said facets may have a substantially coincident focal point or zone.

The lens means may be divided into a series of substantially annular zones each of material having a different wave velocity.

The apparatus may be applied to treatment of a zone of tissue on or beneath the dermis.

According to a second aspect of the present invention, there is provided a method of treatment of tissue comprising the steps of providing an apparatus as described above, having such pre-selected characteristics that the energy is focussable on the zone to be treated, and applying said apparatus to a body within which lies the tissue to be treated.

In order to treat skin blemishes, the tissue to be treated may be subcutaneous blood vessels.

In a cosmetic depilation method, the tissue to be treated may be hair follicles.

In a cosmetic tattoo removal method, the tissue to be treated may be stained skin cells.

Embodiments of the present invention will now be more particularly described by way of example and with reference to the accompanying drawings, in which:—

Examples of apparatus embodying the invention are given below, by way of example and with reference to FIG. 1 of the drawings.

In the Examples, $I_p$ represents the thickness of the lens at its periphery;

$I_c$ represents the thickness of the lens along its axis;

$d_o$ represents the diameter of the lens: and

R represents the radius of curvature of the concave face of the lens.

Figure 1:
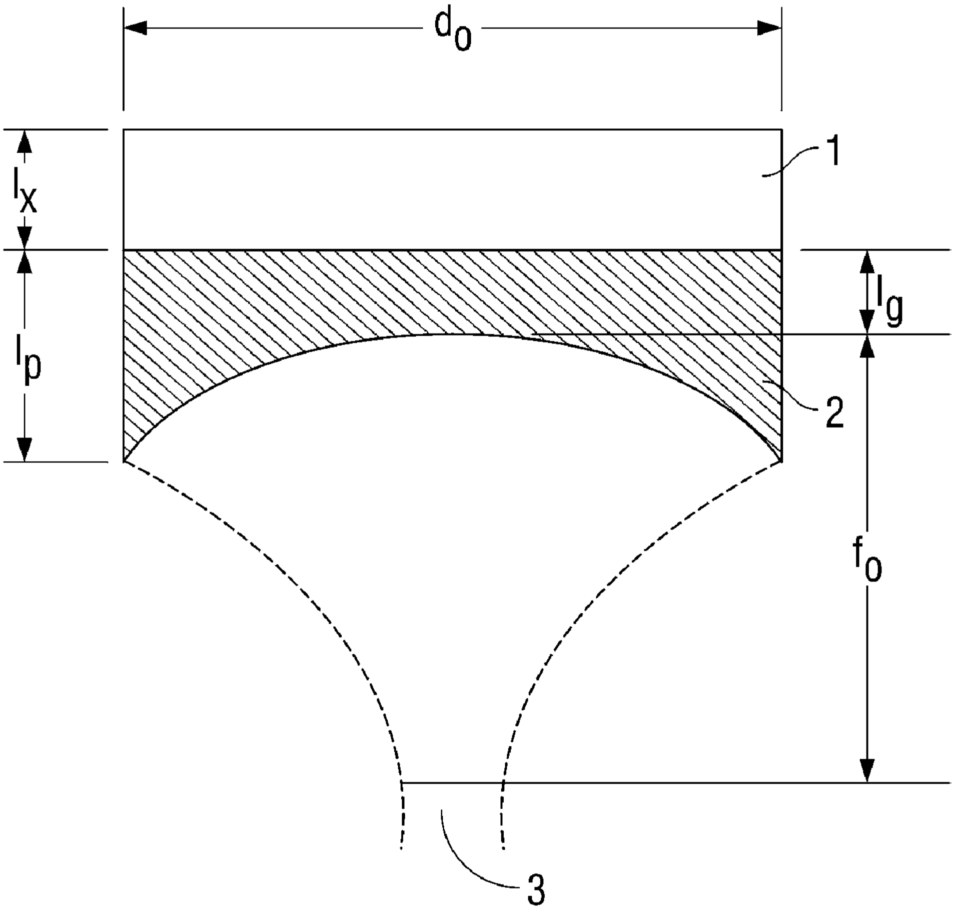
FIG. 1 shows schematically a system for generating focused ultrasound.

Referring now to FIG. 1 of the drawings, a piezoelectric ceramic disc 1 is adapted to produce high frequency ultrasound in the 1-5 MHz range when excited at an appropriate frequency by electrical means (not shown). Immediately adjacent to the piezoelectric ceramic disc 1, and affixed thereto by appropriate adhesive means, is a focusing plano-concave lens 2 of aluminium alloy, titanium alloy or other suitable material or mixture, whereby the ultrasonic vibration is directed to a focal zone 3 within the body wherein is located tissue to be treated.

EXAMPLE 1

An apparatus useful at a frequency in the region of 1.57 MHz had lens dimensions as follows:

$I_p$=4.0 mm $I_c$=1.5 mm $d_o$=10 mm giving an apparatus having a focal length of 7.0 mm and a focal area of 0.02 $cm^2$.

EXAMPLE 2

An apparatus useful at a frequency in the region of 1.55 MHz had lens dimensions as follows:

$I_p$=3.5 mm $I_c$=1.5 mm $d_o$=10 mm

R=7.5 mm giving an apparatus having a focal length of 10.0 mm and a focal area of 0.025 $cm^2$.

EXAMPLE 3

An apparatus useful at a frequency in the region of 1.57 MHz had lens dimensions as follows:

$I_p$=4.0 mm $I_c$=1.5 mm $d_o$10 mm

R=6.26 mm giving an apparatus having a focal length of 7.6 mm and a focal area of 0.02 $cm^2$.

Figure 2:
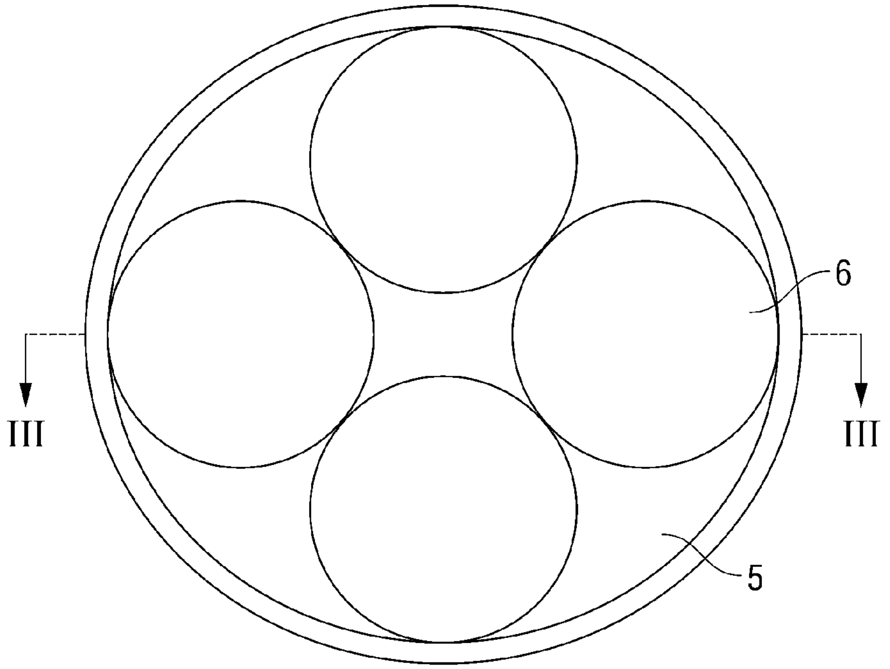
FIG. 2 shows schematically in end elevation a system for generating high intensity focused ultrasound.
Figure 3:
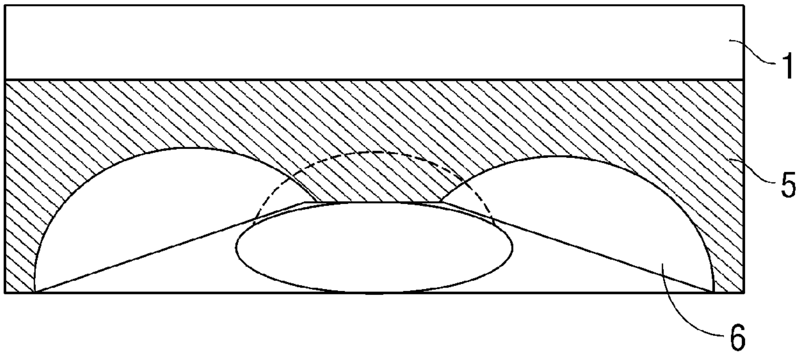
FIG. 3 shows schematically and in cross-section the system of FIG. 2.

Referring now to FIGS. 2 and 3, a single piezoelectric ceramic transducer, preferably of diameter 35 mm, is attached to a complex lens 5, of thickness preferably 12-13 mm at its periphery and in the region of 8 mm at its thinnest point.

The outer surface of the lens 5 is formed to have four equiangularly spaced concavities 6. Each forms part of a sphere, with the radii of curvature meeting at a preselected point.

More or less than four concavities 6 may be provided.

Further Examples of theoretical determination of lens characteristics are given below:

EXAMPLE 4

Results for a physical system of conjoined lens and PZT where:

Thickness of PZT disc—$I_1$=2 mm

Thickness of lens at periphery—$I_2$=7.5 mm

Thickness of lens at axis—$I_3$=1.5 mm

Radius of curvature of lens face—R=15.25 mm

Figure 8:
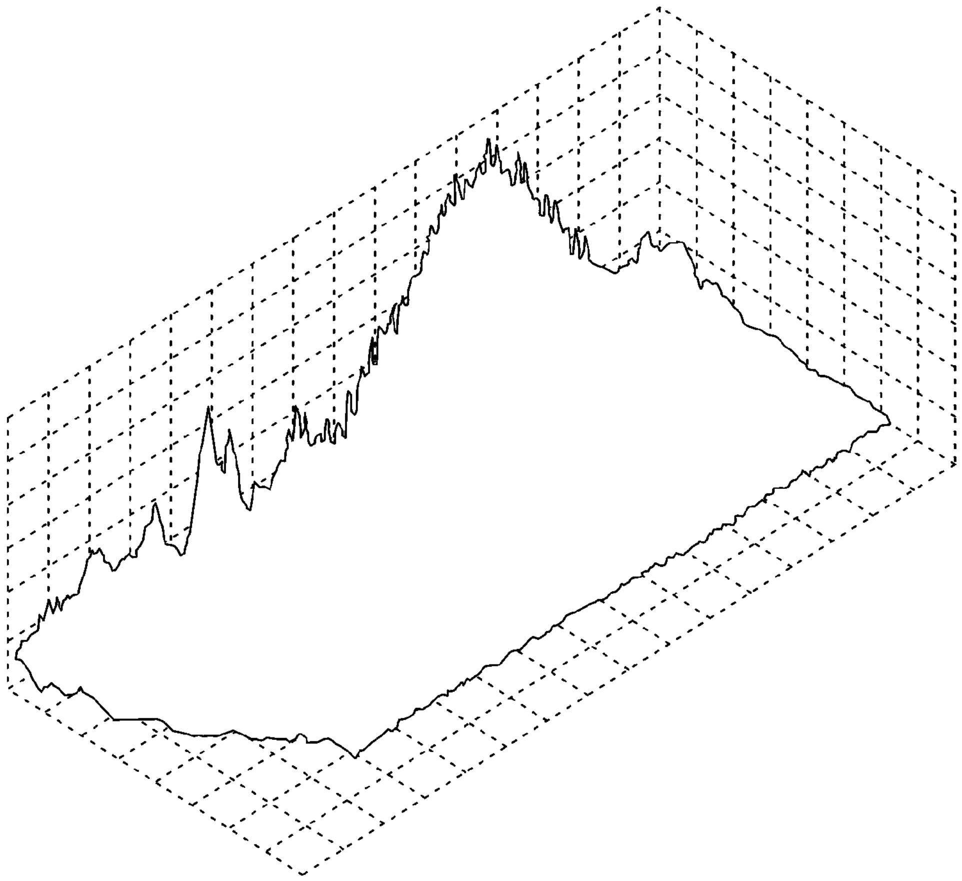
FIG. 8 shows 3D plot of pressure amplitude up to 36 mm from the lens surface over half the radiatory surface, i.e. 12.5 mm from centre line.
Figure 9:
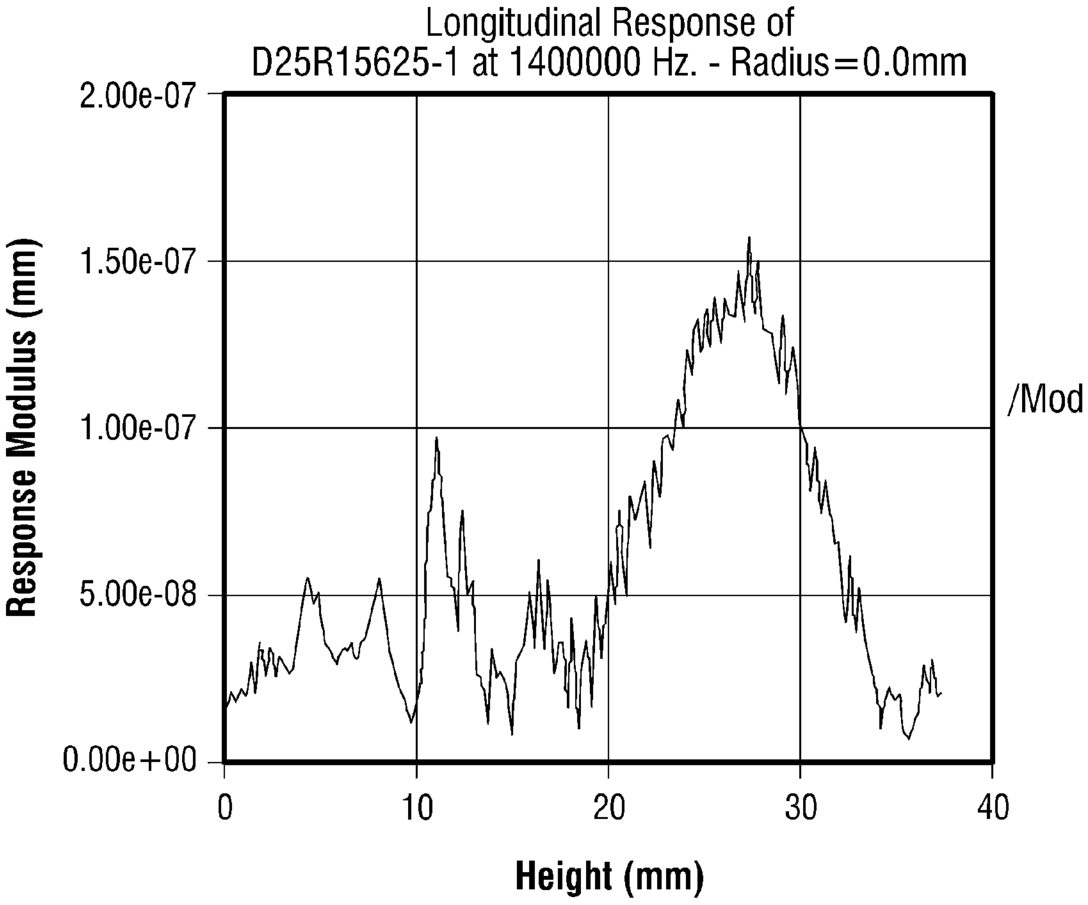
FIG. 9 shows graphically pressure variation along the lens axis showing peak intensity 27 mm from the lens surface.
Figure 10:
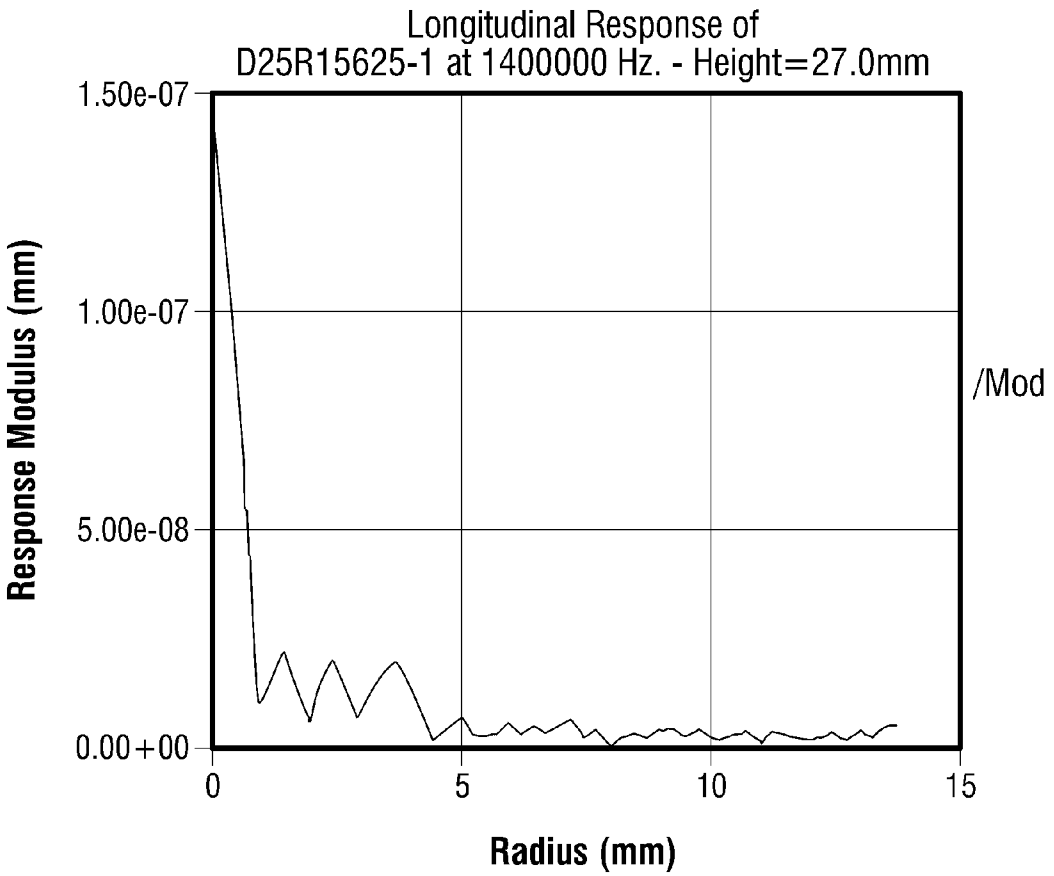
FIG. 10 shows graphically radial variation of intensity of the focal plane.

Diameter of assembly—D=25 mm are shown in FIGS. 8 to 10, where:

FIG. 8 shows 3D plot of pressure amplitude upto 36 mm from the lens surface over half the radiatory surface, i.e. 12.5 mm from centre line;

FIG. 9 shows pressure variation along the lens axis showing peak intensity 27 mm from the lens surface; and FIG. 10 shows radial variation of intensity of the focal plane.

EXAMPLE 5

Results for a physical system of conjoined lens and PZT where:

Thickness of PZT disc—$I_1$=2 mm

Thickness of lens at periphery—$I_2$=4 mm

Thickness of lens at axis—$I_3$=1.5 mm

Radius of curvature of lens face—R=6.25 mm

Figure 5:
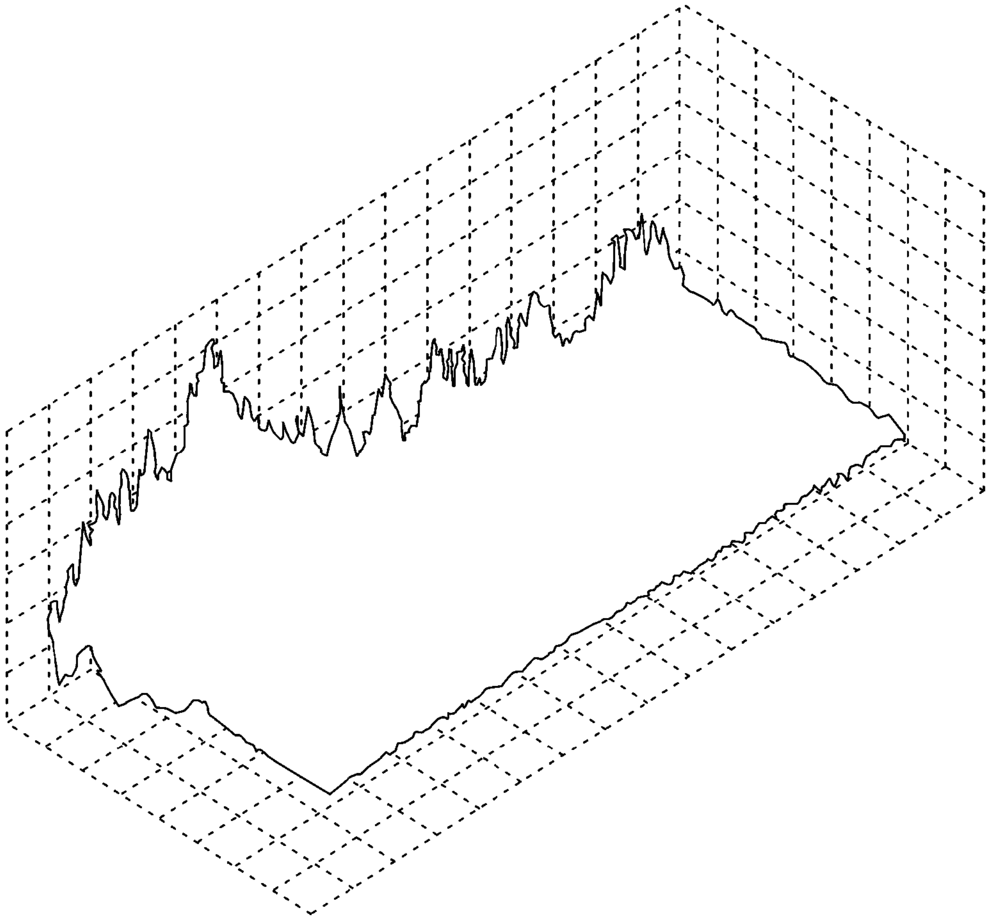
FIG. 5 shows 3D plot of pressure amplitude up to 36 mm from the lens surface over half the radiatory surface, i.e. 12.5 mm from centre line.
Figure 6:
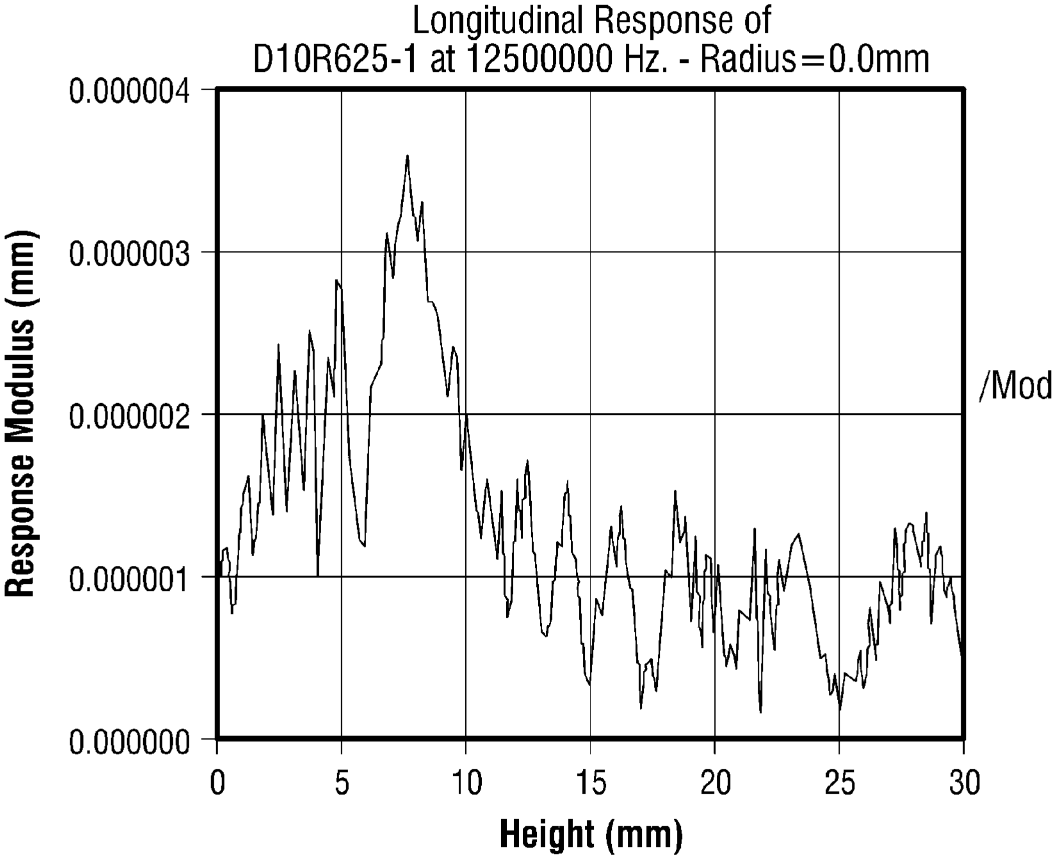
FIG. 6 shows graphically pressure variation along the lens axis showing peak intensity 8 mm from the lens surface.
Figure 7:
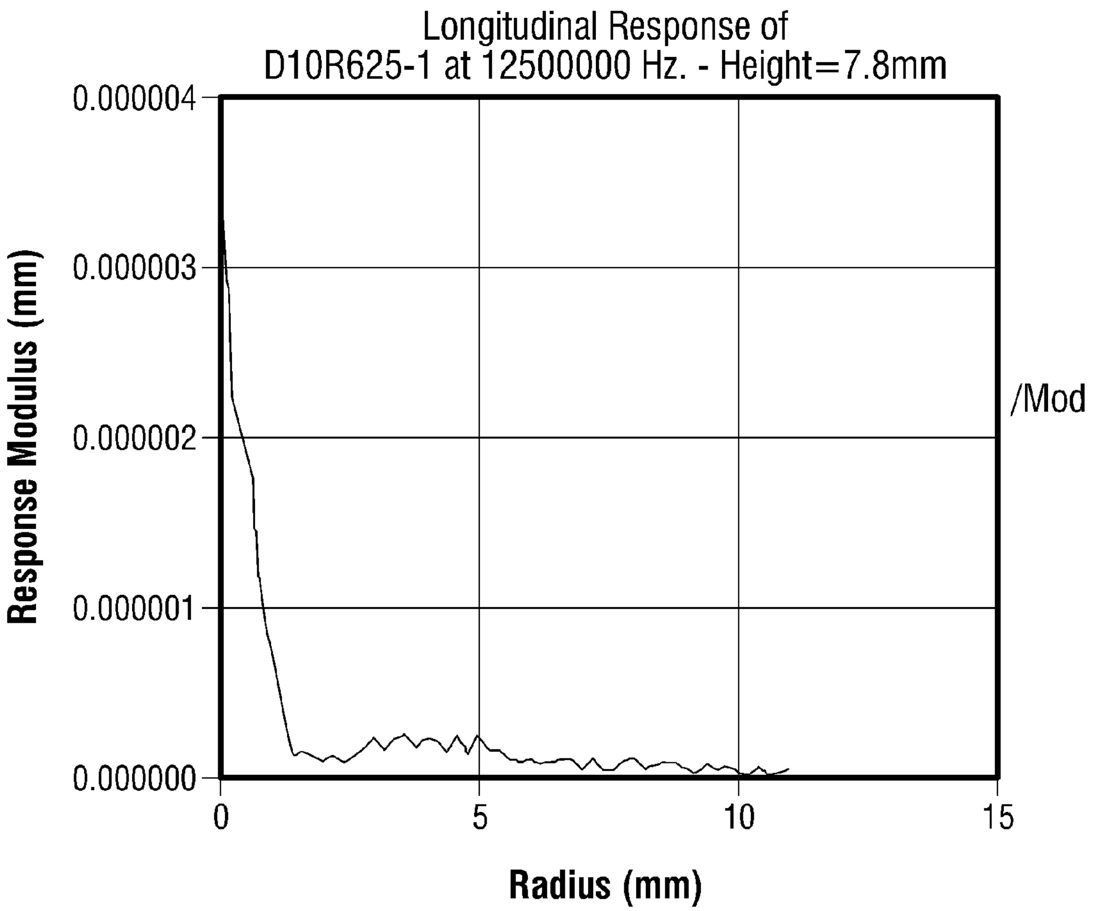
FIG. 7 shows graphically radial variation of intensity of the focal plane.

Diameter of assembly—D=10 mm are shown in FIGS. 5 to 7, where:

FIG. 5 shows 3D plot of pressure amplitude upto 36 mm from the lens surface over half the radiatory surface, i.e. 12.5 mm from centre line;

FIG. 6 shows pressure variation along the lens axis showing peak intensity 27 mm from the lens surface; and FIG. 7 shows radial variation of intensity of the focal plane.

The beam cross section determined experimentally closely matches the theoretically predicted pattern.

When a PZT transducer element is mechanically attached to a focussing device, a complex resonator is created which can only be analysed in its operating mode using sophisticated finite element techniques. Such methods have been refined to permit detailed analysis of the dynamic wave patters transmitted from close coupled duplex focussing transmitters which consist essentially of a plain disc PZT transducer, bonded to a plano-concave metal lens. The theory considers the geometry and acoustic properties of the duplex focussing device and simulates its operation when transmitting into fluid media over a wide range of frequencies. Such devices operate more like axial or radial resonators in longer wavelength systems and involve distortion of the lens which does not occur in optical systems. This technique allows specific focussing characteristics to be selected to satisfy the energy and geometrical requirements of a wide range of surgical procedures.

Measurements were made in a beam plotting tank, in which a hydrophone is suspended within a volume of water into which an ultrasound device transmits. The hydrophone is accurately positioned relative to the transmitter, in three dimensions, using Vernier drives. The sensor measures the pressure developed by the travelling wave passing through the water, and converts this into a voltage signal; this is then plotted on a PC to produce a record of the transmission path shape. The width of the transmission path can be measured at known distances from the centre of the lens, allowing the calculation of the position of the minimum width, i.e. the "focal point"; and the degree of "focus", the ratio of lens surface area, and area of the transmission path at the "focal" plane.

The material used for the lens was aluminium, for the ease of machining and good acoustic properties, and for the bond—standard Araldite (RTM) epoxy adhesive.

The empirical investigation of lens geometry was carried out in two phases, based on the diameter of the PZT's employed. The previously developed ultrasonic radiating devices utilise 10 mm diameter discs, thus the initial range of lenses were based on 010 mm aluminium discs with one face given a concave machined radius of curvature. The initial radii chosen were intended to cover a representative range, and are listed in the table below.

TABLE 1

(all dimensions in mm)

| Radius | Minimum Thickness ($T_L^{Min}$) | Maximum Thickness ($T_L^{Max}$) |
|---|---|---|
| 6.25 | 1.5 | 4.0 |
| 20.0 | 2.5 | 3.14 |
| ∞ (Flat) | 3.0 | 3.0 |
| 7.0 | 1.5 | 3.601 |
| 7.5 | 1.5 | 3.410 |
| 8.0 | 1.5 | 3.255 |

The smallest radius of curvature was derived by taking the half-wavelength at 1 MHz in aluminium (which is ~2.5 mm) and making this the depth of the concave surface. This meant that if the minimum thickness was also 2.5 mm, then theoretically the greatest amplitude at the lens surface would be shown both at the centre and extremity of the surface. The radius of 6.25 mm was simply the result of fixing these dimensions.

Various values of minimum thickness were examined for the first three radii of curvature, but only those listed in Table 1 showed noteworthy results, see Table 2. In light of these results the second three lens types were examined in order to investigate the apparent progress shown by the R6.25 (i.e. 6.25 mm radius of curvature) types.

TABLE 2

(all dimensions in mm)

| Radius | f/MHz | Acoustic Output/mg[1] | Focal Length | Transmission Path Ø | Focussing Factor[2] |
|---|---|---|---|---|---|
| 6.25 | 1.55 | 0 to 3 | 7.7 | 1.9 | 35.91 |
| 20.00 | 1.561 | 3 | 12 | 3.3 | 9.33 |
| 20.00 | 1.605 | 6 | 13 | 2.8 | 12.96 |
| ∞ (Flat) | 1.242 | 4 | 6 | 6.2 | 2.6 |
| 7.00 | 1.57 | 0 to 3 | 8 | 1.9 | 32.54 |
| 7.50 | 1.55 | 0 | 10 | 1.8 | 35.43 |
| 8.00 | 1.562 | — | 7 | 5.6 | 3.58 |

[1]Force Balance measurement

[2]Ratio of area of Transmission Path at Focal Plane to surface area of Lens

The first point to note is the small values obtained for Acoustic Output. This is due to two factors. Firstly, the crystals are "tuned" to a natural frequency of 1 MHz, thus the modes of resonance giving required characteristics are "off-resonance", insofar as they are not at the natural resonant frequency of the systems. This results in poor energy transfer from the generator. Consequently, the generator should be optimised for the loads specific electrical characteristics, allowing modes of resonance not at the natural resonant frequency to be efficiently driven.

The only example of the first group of lenses showing pronounced reduction in Transmission Path Diameter was the R6.25 lens with a minimum thickness of 1.5 mm; those examples not listed failed to show a significant degree of "focus". Whilst the marginal levels of "focus" shown by the R20 (i.e. 20 mm radius of curvature) and Flat examples are not in themselves impressive, they suggested a decrease in the desired characteristics with increasing radius of curvature. Most interestingly of all, the Flat lens still appears to illustrate a modicum of "focus".

These results suggest a diffraction mechanism for the reduction in Transmission Path Diameter. The "focus" shown by the Flat lens may be attributed to a near field effect where destructive and constructive interference between waves transmitted from the surface produce a resultant converged path. The mechanism by which the greater decreases in Transmission Path Diameter are attained are also likely to be based on an interference form, in which case the decrease in radius was responsible for an amplification of this effect.

In order to assess this premise, a second series, this time of 010 (10 mm diameter) lenses, was produced. These investigated the effects of smaller increases in radius from the "optimum" R6.25 form. The results appear to show that a similar level of "focus" can be attained, but that it has a limit, reached with a radius of around 8.0 mm, at which no resonant frequency showed a similarly pronounced "focus".

The following conclusions may be drawn:

The minimum thickness of the lens is preferably approximately 1.5 mm.

The radius of curvature of the lens and diameter of the disc should result in a pronounced depth to the lens.

A generator should be capable of optimal matching to modes other than to the natural frequency of the transducer, since modes of resonance providing the required characteristics are not necessarily coincident with the natural resonant frequency.

These conclusions led to a second phase of the empirical investigation. Ø25 (25 mm diameter) PZT's were affixed to a range of aluminium lenses machined with radii of curvature shown below.

TABLE 3

(all dimensions in mm)

| Radius | Minimum Thickness ($T_L^{Min}$) | Maximum Thickness ($T_L^{Max}$) |
|---|---|---|
| 15.625 | 1.5 | 7.753 |
| 17.5 | 1.5 | 6.753 |
| 20.0 | 1.5 | 5.888 |

These transducers were investigated in the prescribed manner, the results being listed in Table 4.

TABLE 4

(all dimensions in mm)

| Radius | f/MHz | Acoustic Output/mg[1] | Focal Length | Transmission Path Ø | Focussing Factor[2] |
|---|---|---|---|---|---|
| 15.625 | 1.232 | 155 | 19 | 2.1 | 177.38 |
| 15.625 | 1.242 | 285 | 23 | 1.8 | 241.18 |
| 15.625 | 1.334 | 120 | 12.5 | 3.8 | 54.12 |
| 17.50 | 1.405 | 130 | 20 | 2.1 | 166.92 |
| 20 | 1.255 | 180 | 24 | 4.2 | 39.81 |
| 20 | 1.436 | 35 | 24 | 2.0 | 175.59 |
| 20 | 1.492 | 10 | 22 | 2.1 | 159.35 |

[1]Force Balance measurement
[2]Ratio of area of Transmission Path at Focal Plane to surface area of Lens The results listed in Table 4 show a dramatic increase in "focus" over those values measured for the Ø10 series of transducers. The increased acoustic output of the systems, compared to earlier, is also noticeable.

The levels of "focus" measured are of the order needed to reach the intensities required to achieve denaturing in mammalian tissue. This achievement was the initial requirement to move on to identify the levels of Heat Generator in samples of "model" absorbing material.

The experimental technique and principal of the set-up is quite simple. The transmitter being assessed is inserted into a lower holding tube, to a known depth. Water is injected into the space between the lens and the membrane covering the tube, all air being removed via a second tube/syringe. The upper portion of the system is mounted against the lower. The sample holder, containing the chosen absorbing material held in by a second membrane, is screwed down to the required height. Acoustic coupling gel acts as a lubricant between the two membranes and limits losses. The thermocouple holder is inserted into the top of the sample holder to measure initial temperature, it is then removed, the transducer activated for a fixed time, and the thermocouple re-introduced to measure the temperature rise due to the insonation. (Ambient temperature is simultaneously monitored as a control).

The results, for absorption of energy transmitted from the Ø25, R15.625, $T_L^{Min}$ 1.5 transducer, obtained in triethylene glycol (TEG), liver and a mixture of the two, are presented below.

TABLE 5

| Absorbing Material | Distance/ mm[1] | Temperature Increase/° C. |
|---|---|---|
| TEG | 23 | 19 |
| Liver(water) | 18 | 12 |
| Liver(TEG) | 18 | 14 |

[1]Distance from centre of lens to interface of membranes.

These results quoted are not the complete picture. The pattern of temperature rise, over a range of distances from the lens, does not smoothly rise to a maximum and then recede, it goes through a number of peaks and troughs. This is almost certainly due to the complicated nature of the transmission within the experimental cell.

The nature of the material noted in Entry 1 allows an energy balance to be carried out whereby a measure of the efficiency of the process can be measured:

| | | |
|---|---|---|
| Acoustic Output from Transducer = | 0.285/0.0688 = | 4.142 W |
| Energy Transmitted during 5s insonation = | 4.142 x 5 = | 20.71 J |
| Average Energy Absorbed by TEG = | 2.4 x 0.5625 x 15 = | 20.25 J |
| Efficiency of Insonation Process = | 20.25/20.71 = | 97.8% |

Thus, TEG is an excellent test material for assessment of Acoustic Absorption.

In order to optimise the focussing effect of the close coupled generators, the propagation of wave energy from all parts of the concave output face should be directed substantially towards the generator axis, and each surface element of the concave radiating face should experience a displacement which is substantially in-phase with all neighbouring elements, in both circumferential and radial directions.

These criteria can be met by consideration of the fact that different materials have individual acoustic properties, and the requisite level of control can be achieved by appropriate selection of materials.

Figure 4A:
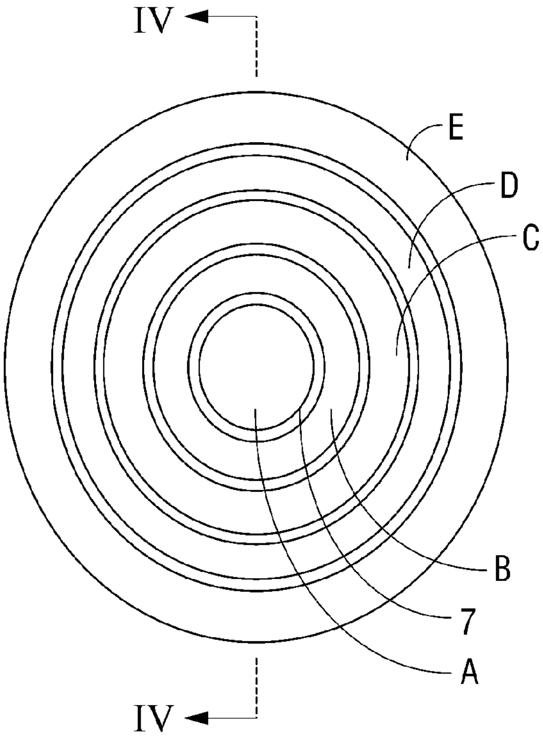
FIGS. 4A and 4B shows schematically, in elevation and in cross section a composite system incorporating differential phase shift lens.

Referring now to FIG. 4A, there is shown a device in which the plano-concave lens comprises a plurality of annular sections (B, C, D, E) surrounding a central circular section (A). Each section is of a material having complimenting properties so that the wave from the planar face, contacting the PZT disc, will be transmitted from the concave radiating face 8 in an optimum manner.

Figure 4B:
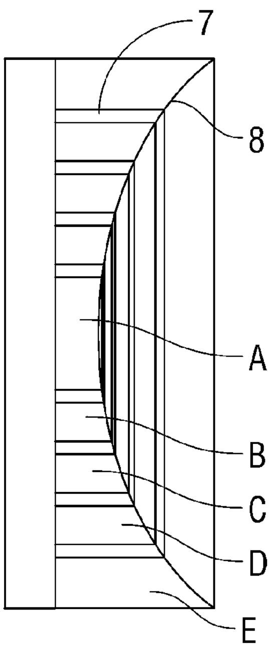

The device shown in FIGS. 4A and 4B has concentric sections A, B, C, D and E, consisting of different materials each displaying an appropriate phase velocity constant, and separated by tubes 7 of an isolating material, for example PTFE. The elements of the concave, radiating surface 8 are adapted to meet the above criteria, i.e. with in-phase convergent waves transmitting from surface 8. Table 6, below shows by way of example materials and thei arrangement to give increasing phase velocity from the inner to the outer elements to compensate for the increase in thickness across the lens.

TABLE 6

| Element | Material | Acoustic Velocity/cms$^{-1}$ |
|---|---|---|
| A | Aluminium Bronze | 4.07 |
| B | K-Monel | 4.3 |
| C | Ti Alloy | 4.78 |
| D | Alumina | 5.01 |
| E | Stainless Steel | 5.16 |

Optimum drive frequencies and annular widths consistent with a particular focussing radius can be determined.

The advantages of this method of construction and design of the apparatus include:

1. Increased mechanical strength of the PZT lens structure.
2. Higher energy output per unit size.
3. Greater design flexibility.
4. Reduced unit cost.
5. Use of multi-head systems to create unique beam shapes.

The described embodiments of the present invention are intended to be illustrative rather then restrictive, and are not intended to represent every embodiment of the present invention. Various modifications and variations can be made without departing from the spirit or scope of the invention as set forth in the following claims both literally and in equivalents recognized in law.

The invention claimed is:

1. An apparatus for focusing a beam of ultrasonic vibration comprising means to generate ultrasonic vibrations and lens means affixed to said generating means and adapted to focus said ultrasonic vibration at a predetermined zone, wherein the lens means is divided into a plurality of regions each of which comprises material having a wave velocity different from that of adjacent regions, wherein at least two adjacent regions comprise of different materials, said different materials each displaying an appropriate phase velocity constant, and separated by tubes of an isolating material, and wherein an inner region of said at least two adjacent regions has a lower phase velocity than an outer region of said at least two adjacent regions so that said ultrasonic vibrations transmitted from said at least two adjacent regions are in-phase and convergent.

2. An apparatus as claimed in claim 1, wherein the lens means is plano-concave.

3. An apparatus as claimed in claim 1, wherein the lens means comprises titanium, titanium alloy, aluminum, aluminum alloy, or a mixture containing any one or more of such materials.

4. An apparatus as claimed in claim 1, wherein the lens means comprises a plurality of individual lens facets.

5. An apparatus as claimed in claim 4, wherein the plurality of individual lens facets is affixed to a single generating means.

6. An apparatus as claimed in claim 4, wherein at least one of said facets have a substantially coincident centre of its radius of curvature.

7. An apparatus as claimed in claim 4, wherein at least one of said facets have a substantially coincident focal point.

8. An apparatus as claimed in claim 1, wherein the plurality of regions are divided into a series of substantially annular regions.

9. A method of treatment of tissue comprising the steps of:

providing an apparatus for focusing a beam of ultrasonic vibration comprising means to generate ultrasonic vibrations and lens means affixed to said generating means and adapted to focus said ultrasonic vibration at a predetermined zone, wherein the lens means is divided into a plurality of regions each of which comprises material having a wave velocity different from that of adjacent regions, wherein at least two adjacent regions comprise of different materials, said different materials each displaying an appropriate phase velocity constant, and separated by tubes of an isolating material, and wherein an inner region of said at least two adjacent regions has a lower phase velocity than an outer region of said at least two adjacent regions so that said ultrasonic vibrations transmitted from said at least two adjacent regions are in-phase and convergent; and providing said apparatus with pre-selected characteristics that the energy is focusable on a zone of tissue to be treated; and applying said apparatus to a body within which lies said zone.

10. A method as claimed in claim 9, wherein the lens means is plano-concave.

11. A method as claimed in claim 9, wherein the lens means comprises titanium, titanium alloy, aluminum, aluminum alloy, or a mixture containing any one or more of such materials.

12. A method as claimed in claim 9, further comprising the step of providing the lens means with a plurality of individual lens facets.

13. A method as claimed in claim 12, further comprising the step of affixing the plurality of individual lens facets to a single generating means.

14. A method as claimed in claim 12, wherein at least one of said facets have a substantially coincident centre of their radius of curvature.

15. A method as claimed in claim 12, wherein at least one of said facets have a substantially coincident focal point.

16. A method as claimed in claim 9, wherein the plurality of regions are divided into a series of substantially annular regions.

* * * * *